United States Patent [19]

Collins et al.

[11] 3,965,143

[45] June 22, 1976

[54] 16-OXYGENATED PROSTANOIC ACID DERIVATIVES

[75] Inventors: Paul W. Collins, Deerfield; Raphael Pappo, Skokie, both of Ill.

[73] Assignee: G. D. Searle & Co., Chicago, Ill.

[22] Filed: Mar. 26, 1974

[21] Appl. No.: 454,913

[52] U.S. Cl. .................. 260/468 D; 260/240 R; 260/345.7; 260/345.8; 260/347..3; 260/347.4; 260/410.9 R; 260/413; 260/438.1; 260/448.8 R; 260/488 R; 260/514 D; 260/632 Y; 424/305; 424/317
[51] Int. Cl.² .................. C07C 61/38; C07C 69/74
[58] Field of Search .................. 260/465 D, 514 D

[56] References Cited
UNITED STATES PATENTS 3,812,172   5/1974   Bundy .......................... 260/468

FOREIGN PATENTS OR APPLICATIONS 7,203,126   9/1972   Netherlands .................. 260/468
7,310,276   1/1974   Netherlands .................. 260/468

OTHER PUBLICATIONS

I guchi et al, Prostaglandins, 4 535 (1973).

*Primary Examiner*—Robert Gerste
*Attorney, Agent, or Firm*—John A. Dhuey

[57] ABSTRACT

16-Oxygenated prostanoic acid derivatives, displaying valuable pharmacological properties, e.g. gastric antisecretory, are produced by reaction of an (optionally 3-oxygenated)-5-oxocyclopent-1-enealkanoic/alkenoic acid or ester with the appropriate organometallic reagent.

3 Claims, No Drawings

16-OXYGENATED PROSTANOIC ACID DERIVATIVES

The present invention is concerned with novel 16-oxygenated prostanoic acid derivatives represented by the following structural formula

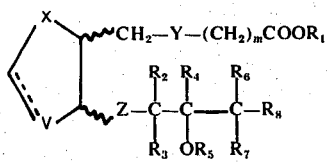

wherein $R_1$, $R_2$, $R_3$, $R_4$, $R_6$ and $R_7$ can be hydrogen or a lower alkyl radical, $R_5$ can be hydrogen or a lower alkanoyl, tetrahydrofuranyl, tetrahydropyran-2-yl, tri(-lower alkyl)silyl or lower alkyl radical, X is a carbonyl, hydroxymethylene or (lower alkanoyl)oxymethylene radical, V is a methylene, hydroxymethylene, (lower alkanoyl)oxymethylene, tetrahydrofuranyloxymethylene, tetrahydropyran-2-yloxymethylene or tri-(lower alkyl)silyloxymethylene radical, Y is an ethylene, cis-vinylene or trans-vinylene group, Z is an ethylene, cis-vinylene, trans-vinylene or ethynylene radical, the wavy lines denote the alternative α and β stereochemical configurations, the dotted line indicates an optional double bond, m is an integer greater than 2 and less than 5 and $R_8$ is an alkyl group containing 3–5 carbon atoms or a cycloalkyl group containing 5–7 carbon atoms.

The lower alkyl radicals represented in the foregoing structural formula are typified by methyl, ethyl, propyl, butyl, pentyl, hexyl, heptyl and the branched-chain radicals thereof.

Typical of the lower alkanoyl radicals denoted in that formula are formyl, acetyl, propionyl, butyryl, valeryl, caproyl, heptanoyl, and the branched-chain radicals corresponding.

The cycloalkyl groups denoted above are typified by cyclopentyl and cyclohexyl.

The novel compounds of the present invention display valuable pharmacological properties as is exemplified by their ability to inhibit the gastric secretion stimulated by secretogogues such as histamine and pentagastrin while furthermore possessing the surprising advantage of lacking the potent undesirable side-effects displayed by related substances. In addition, these compounds are inhibitors of blood platelet aggregation and, moreover, display anti-fertility and bronchodilating properties.

The specific assay used to detect gastric anti-secretory activity is described as follows.

Adult female beagle dogs weighing 13–20 kg. are prepared with denervated fundic Heidenhain pouches. After a recovery period of at least 4 weeks following surgery, the animals are fasted for approximately 20 hours, then are placed in Pavlov stands and infused intravenously with saline solution. The pouched secretions are collected every 15 minutes and measured for volume and total acidity by titration with 0.1N sodium hydroxide to pH 7.0. Following a 30 minute basal secretion the dogs are infused with a saline solution of histamine dihydrochloride at a dose of 1.0 mg./hr. The volume of the diffusion is kept at approximately 13 ml./hr. A steady state plateau of gastric secretion is obtained approximately 1 hour following the start of histamine infusion, at the end of which time the test compound dissolved in an ethanolic iso-osmotic phosphate buffer solution is administered by a single intravenous injection. The duration of the anti-secretory effects is determined and the side-effects, if any, recorded. The compound is rated active if statistically significant inhibition of secretory parameters occur following compound treatment.

Starting materials suitable for use in the manufacture of the compounds of the present invention are the cyclopent-1-enealkanoic/alkenoic acids and esters of the following formula

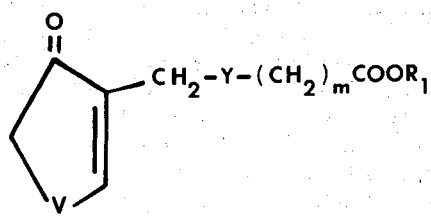

wherein $R_1$, Y, V and m are as defined hereinbefore. Introduction of the oxygenated alkenyl or oxygenated alkynyl side chain at the 2-position of the cyclopentane ring is effected by reaction with a suitable organometallic reagent. Particularly suitable reagents for introduction of the oxygenated alkenyl side chain are the alkenyl coppers and the lithium alkenyl cuprates prepared from the appropriate unsaturated alcohol. A convenient method for manufacture of the cuprate reagent comprises the reaction of an acetylenic alcohol of the following formula

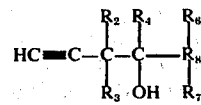

wherein $R_2$, $R_3$, $R_4$, $R_6$, $R_7$ and $R_8$ are as hereinbefore defined, with a trialkylsilyl halide to afford the corresponding trialkylsilyl ether, addition of catechol borane across the acetylenic bond to produce the boronic acid derivative, reaction of the latter substance with iodine to yield the 1-alkenyl iodide, which is contacted with a cuprous acetylide and a lithium alkyl to afford the desired lithium cuprate reagent. The latter processes are exemplified by the reaction of 1-octyn-4-ol with tertiary-butyldimethylsilyl chloride to afford 1-octyn-4-ol tertiary-butyldimethylsilyl ether, reaction of that ether with catechol borane to yield 4-tertiary-butyldimethylsilyloxy-trans-1-octenyl boronic acid, which is contacted with iodine to produce 4-tertiary-butyldimethylsilyloxy-trans-1-octenyl iodide. That halide is then allowed to react with n-butyl lithium and cuprous 1-pentynylide, thus affording racemic lithium [(1-pentynyl)-(4-tertiary-butyldimethylsilyloxy-trans-1-octenyl)cuprate].

Reaction of the latter cuprate reagents with the aforementioned starting materials of the following formula

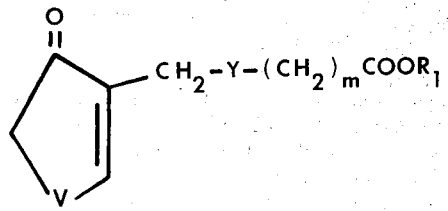

the manufacture of which compounds is detailed in Pappo and Jung U.S. Pat. No. 3,558,682, issued Jan. 26, 1971, and in Bruhn and Pappo U.S. Patent application Ser. No. 346,358, filed Mar. 30, 1973, results in introduction of the oxygenated alkenyl side chain at the 2-position of the cyclopentane ring. As a specific example, racemic methyl 7-(3-tetrahydropyran-2-yloxy-5-oxocyclopent-1-ene)heptanoate is allowed to react with racemic lithium [(1-pentynyl)-(4-tertiary-butyldimethylsilyloxy-trans-1-octenyl)cuprate], thus affording racemic methyl 7-[(3(R)-tetrahydropyran-2-yloxy)-2β-(4(RS)-tertiary-butyldimethylsilyloxy-trans-1-octenyl)-5-oxocyclopentane]-1α-heptanoate. Removal of the trialkylsilyl and tetrahydropyran-2-yl protecting groups is conveniently effected by reaction with acetic acid, thus producing a 1:1 mixture of racemic methyl-7-[3(R)-hydroxy-2β-(4(R)-hydroxy-trans-1-octenyl)-5-oxocyclopentane]-1α-heptanoate and racemic methyl 7-[3(R)-hydroxy-2β-(4(S)-hydroxy-trans-1-octenyl)-5-oxocyclopentane]-1α-heptanoate, which diastereoisomers are separated by high pressure liquid chromatographic techniques.

Additional copper agents suitable for use in the manufacture of the instant compounds are the lithium divinyl cuprates and the vinyl coppers of the type described by Kluge et al., *J. Amer. Chem. Soc.*, 94, 7827 (1972), the lithium vinyl cyano cuprates of the type described by Gorlier et al., *Chem. Comm.*, 3, 88 (1973) and the lithium diorganocuprates as described by Mandeville et al., *J. Org. Chem.*, 39, 400 (1974).

Reaction of the aforementioned cyclopent-1-enealkanoic/alkenoic acid and ester starting materials with an aluminum alkenyl organometallic reagent results in the instant compounds wherein the oxygenated function at the 3-position of the cyclopentane ring is in the epi stereochemical configuration. Typically, 4(RS)-4-methyl-1-octyn-4-ol is converted to the corresponding triethylsilyl ether by reaction with triethylsilyl chloride and that ether is contacted with diisobutylaluminum hydride to produce the aluminum alkenyl reagent. The latter reagent is allowed to react with methyl 3-hydroxy-5-oxocyclopent-1-eneheptanoate, thus affording the racemic methyl 7-[3(S)-hydroxy-2β(4(RS)-4-methyl-4-triethylsilyloxy-trans-1-octenyl)-5-oxocyclopentane]-1α-heptanoates.

The aluminum alkynyl organometallic reagents are particularly useful for manufacture of the instant alkynyl derivatives wherein the oxygenated function at the 3-position of the cyclopentane ring is in the epi stereochemical configuration. Thus, 4(RS)-1-octyn-4-ol tertiary-butyldimethylsilyl ether is contacted first with n-butyl lithium, then with dimethylaluminum chloride to afford dimethyl-4(RS)-tertiary-butyldimethyl-silyloxy-1-octynyl aluminum and the latter reagent is allowed to react with methyl 3-hydroxy-5-oxocyclopent-1-eneheptanoate, thus affording, after removal of the protecting group by acid treatment, the racemic methyl 7-[3(S)-hydroxy-2β-(4(RS)-hydroxy-1-octynyl)-5-oxocyclopentane]-1α-heptanoates.

The mono and/or di-acylated derivatives of the present invention are conveniently produced by reaction of the corresponding hydroxy substances with a lower alkanoic acid anhydride or halide, preferably in the presence of a suitable acid acceptor such as pyridine or triethylamine. As a specific example, the aforementioned racemic methyl 7-[3(R)-hydroxy-2β-(4(S)-hydroxy-trans-1-octenyl)-5-oxocyclopentane]-1α-heptanoate is contacted with acetic anhydride and pyridine, thus affording racemic methyl 7-[3(R)-acetoxy-2β-(4(S)-acetoxy-trans-1-octenyl)-5-oxocyclopentane]-1α-heptanoate.

The instant compounds characterized by a cycloalkyl group in the substituent at the 2-position of the cyclopentane ring are produced according to the processes described hereinbefore, wherein the appropriate cycloalkyl acetylenic alcohols are used as the starting materials. 4(RS)-4-Cyclohexylmethyl-4-methyl-1-butyn-4-ol thus is obtained by the reaction of methyl cyclohexylmethyl ketone with 1-propynyl magnesium bromide and is converted to the triethylsilyl ether by reaction with triethylsilyl chloride. The cuprate reagent is prepared from that ether by the processes described hereinbefore, thus affording racemic lithium [(1-pentynyl)-4(RS)-4-cyclohexylmethyl-4-methyl-4-triethylsilyloxy-trans-1-butenyl cuprate]. Reaction of that reagent with methyl 7-[3(RS)-tetrahydropyran-2-yloxy-5-oxocyclopent-1-ene]heptanoate, followed by cleavage of the triethylsilyl and tetrahydropyran-2-yl protecting groups by the process described hereinbefore, results in racemic methyl 7-[3(R)-hydroxy-2β-(4(RS)-cyclohexylmethyl-4-hydroxy-4-methyl-trans-1-butenyl-5-oxocyclopentane]-1α-heptanoate.

The compounds of the present invention containing a double bond at the 3(4) position of the cyclopentane ring are readily produced by dehydration of the corresponding 3-hydroxy substances. Typically, racemic methyl 7-[3(R)-hydroxy-2β-(4(RS)-hydroxy-trans-1-octenyl)-5-oxocyclopentane]-1α-heptanoate is heated with 90% acetic acid to yield racemic methyl 7-[2β-(4(RS)-hydroxy-trans-1-octenyl)-5-oxocyclopent-3-ene]-1α-heptanoate.

The optically active compounds of this invention are preferably produced by coupling of the optically active 3-oxygenated 5-oxocyclopent-1-enealkanoates or 3-oxygenated 5-oxocyclopent-1-enealkenoates with the copper reagents derived from the optically active acetylenic alcohols. Resolution of the acetylenic alcohols is conveniently achieved by reaction with phthalic anhydride to form the monophthalate ester followed by reaction of that ester with an optically active amine, e.g. (−) or (+) -α-methylbenzylamine, (−) or (+) -α-(1-naphthyl)ethylamine, to form a mixture of the diastereomeric salts, which are separated by fractional crystallization. The 3-oxygenated 5-oxocyclopent-1-enealkanoates and 3-oxygenated 5-oxocyclopent-1-enealkenoates are resolved by reaction with an optically active aminoxycarboxylic acid to afford the 2-diastereomeric oximes, which are separated chromatographically. Cleavage of the oxime moiety by acid treatment affords the individual 3(R) and 3(S) stereoisomers. Thus, for example, when methyl 7-[3(S)- hydroxy-5-oxocyclopent-1-ene]heptanoate and 1-octyn-4(S)-ol are used as the starting materials in the processes described hereinbefore, methyl 7-[3(S)-hydroxy-2β-(4(S)-hydroxy-trans-1-octenyl)-5-oxocyclopentane]-1α-heptanoate is produced.

The invention will appear more fully from the examples which follow. These examples are given by way of illustration only and are not to be construed as limiting the invention either in spirit or in scope as many modifications both in materials and in methods will be apparent from this disclosure to those skilled in the art. In these examples, temperatures are given in degrees Centigrade (°C.) and quantities of materials in parts by weight unless otherwise noted.

EXAMPLE 1

14.85 Parts of 5-chloropent-1-yne is dissolved in 250 parts by volume of toluene and the resulting solution is cooled to approximately −40°. To that solution is then added 62.8 parts by volume of 2.31 M ethereal butyl lithium and stirring is continued for approximately 15 minutes. 6.87 Parts of boron trifluoride etherate is added and the reaction mixture is stirred for about two hours, then is allowed to stand for about 16 hours at −5° to −10°. At the end of that time, 10.14 parts of methyl vinyl ketone is added at −40° and the reaction mixture is stirred for about 4 hours, then is quenched with water. 50 Parts by volume of 3 N hydrochloric acid is added and the mixture is kept at room temperature for about 16 hours, at the end of which time the aqueous and organic layers are separated. The aqueous layer is extracted with toluene and the organic layer with water. The organic solutions are combined, washed successively with aqueous sodium hydroxide and water, then dried over anhydrous sodium sulfate and stripped to dryness under reduced pressure, thus affording the crude product. This material is purified by distillation under reduced pressure to afford 9-chloro-5-nonyn-2-one, boiling at about 80°–92° at a pressure of 0.11–0.06 mm.

EXAMPLE 2

To a solution consisting of 2.77 parts of 9-chloro-5-nonyn-2-one in 8 parts by volume of ethanol is added a solution containing 2.77 parts of sodium cyanide, dissolved in 4 parts of water. The resulting reaction mixture is heated at 80°–100° for about 24 hours, then is cooled and diluted with ether, whereupon 20 parts by volume of dilute aqueous sodium hydroxide is added with stirring. The layers are separated and the alkaline layer is extracted with ether. The ether extracts are combined, then washed with water, dried over anhydrous sodium sulfate and concentrated under reduced pressure to afford 9-cyano-5-nonyn-2-one. This compound exhibits an infrared absorption maximum at 2250 reciprocal centimeters and nuclear magnetic resonance peak at δ2.81 and δ2.50.

EXAMPLE 3

A mixture consisting of 1.79 parts of 9-cyano-5-nonyn-2-one, 5 parts by volume of ethanol and 5 parts by volume of 5% aqueous sodium hydroxide is heated just below the reflux temperature for about 6 hours, then is cooled and extracted with chloroform. The alkaline layer is acidified by means of hydrochloric acid to pH 4, resulting in separation of a brown liquid. This material is extracted with chloroform and the chloroform solution is washed with water, dried over anhydrous sodium sulfate, then concentrated to dryness under reduced pressure to afford 9-oxo-5-decynoic acid. It exhibits nuclear magnetic resonance peaks at δ2.18 and δ2.50.

EXAMPLE 4

To a solution of 23.6 parts of 9-oxo-5-decynoic acid in a mixture of 999 parts by volume of benzene and 221.4 parts by volume of 1% quinoline in benzene is added 1.18 parts of 5% palladium-on-barium sulfate catalyst and the resulting mixture is shaken with hydrogen at atmospheric pressure and room temperature until 1 molecular equivalent of hydrogen is absorbed. The catalyst is then removed by filtration and the filtrate is washed successively with dilute hydrochloric acid and water, then dried over anhydrous sodium sulfate, and stripped of solvent under reduced pressure, thus producing 9-oxo-5-cis-decenoic acid, which exhibits nuclear magnetic resonance maxima at δ2.13 and δ5.39.

EXAMPLE 5

A solution of potassium tertiary-butoxide is prepared by dissolving 4.8 parts of potassium metal in 30 parts by volume of tertiary-butyl alcohol, at reflux temperature under nitrogen. To that solution is then added a solution consisting of 3.7 parts of 9-oxo-5-cis-decenoic acid and 7.23 parts of dimethyl oxalate dissolved in 25 parts by volume of tertiary-butyl alcohol. The addition is conducted with stirring at the reflux temperature. After the reaction mixture is refluxed under nitrogen for about 2½ hours, the colored supernatant is decanted and the precipitate is dissolved in water, then acidified with dilute hydrochloric acid. Extraction of that acidic mixture with chloroform affords an organic solution, which is washed with saturated aqueous sodium chloride, then dried over anhydrous sodium sulfate and stripped of solvent under reduced pressure to afford 7-(2,3,5-trioxo-4-methoxyalylcyclopentane)hept-5-cis-enoic acid, melting at about 99°–104°.

EXAMPLE 6

A mixture consisting of 10.6 parts of 7-(2,3,5-trioxo-4-methoxalylcyclopentane)hept-5-cis-enoic acid and 490 parts by volume of dilute hydrochloric acid is heated at the reflux temperature for about 3 hours, then is cooled and extracted with ethyl acetate. The organic extract is washed with saturated aqueous sodium chloride, then dried over anhydrous sodium sulfate and stripped of solvent under reduced pressure to afford the crude product. Purification of that material is effected by adsorption on a silicic acid chromatographic column followed by elution with ethyl acetate-benzene. From the eluate there are obtained pale yellow crystals of 7-(2,3,5-trioxocyclopentane)hept-5-cis-enoic acid, melting at about 84°–85°.

EXAMPLE 7

A solution of 0.54 part of 7-(2,3,5-trioxocyclopentane)hept-5-cis-enoic acid in 11 parts of water is neutralized by the addition of dilute aqueous sodium hydroxide and that neutralized solution is cooled to 0°–5°, at which point 0.037 part of sodium borohydride is added. The reaction mixture is stirred at 0°–5° for about 50 minutes, then is quenched by the addition of dilute hydrochloric acid to pH 1. The resulting solution is extracted several times with ethyl acetate. The ethyl acetate extracts are combined, washed with saturated aqueous sodium chloride, dried over anhydrous sodium sulfate and concentrated to dryness under reduced pressure to afford white crystals of 7-(2,5-dioxo-3(RS)-hydroxycyclopentane)hept-5-cis-enoic acid, melting at about 83°–85°.

EXAMPLE 8

To a solution of 2.9 parts of 7-(2,5-dioxo-3(RS)-hydroxy-cyclopentane)hept-5-cis-enoic acid in 33.8 parts by volume of methanol, under nitrogen, is added, with stirring, 10.18 parts by volume of acetone dimethyl ketal followed by 3.97 parts by volume of 1.14% methanolic hydrogen chloride. The resulting reaction mixture is allowed to stand at room temperature for about 48 hours, then is stripped of solvent by distillation under reduced pressure. A small amount of ether is added and the mixture is allowed to stand for about 48 hours, then is dissolved in benzene containing 1% triethylamine and that solution is washed successively with dilute aqueous potassium carbonate and water, then dried over anhydrous sodium sulfate and stripped of solvent under reduced pressure to afford white crystals of methyl 7-(4(RS)-hydroxy-2-methoxy-5-oxocyclopent-1-ene)hept-5-cis-enoate, melting at about 77°–78°. It exhibits nuclear magnetic resonance maxima at $\delta 3.69$, $\delta 3.98$, $\delta 4.29$ and $\delta 5.39$.

EXAMPLE 9

To a solution of 0.256 part of methyl 7-(4(RS)-hydroxy-2-methoxy-5-oxocyclopent-1-ene)hept-5-cis-enoate in a mixture consisting of 3.7 parts by volume of tetrahydrofuran and 4.4 parts by volume of toluene, under nitrogen, is added dropwise at $-70°$, 0.33 part by volume of a 3.3 M sodium dihydro bis-(2-methoxyethoxy)aluminate in benzene solution. Stirring is continued at that temperature for about 5½ hours, at the end of which time the reaction mixture is quenched by the addition of methanol. After an additional 10 minute stirring period, the mixture is allowed to warm to room temperature, then is acidified to pH 2 by the addition of dilute hydrochloric acid. The resulting two-phase mixture is extracted with ethyl acetate and the organic extract is washed with saturated aqueous sodium chloride, then dried over anhydrous sodium sulfate under reduced pressure to afford the crude product. That material is purified by adsorption on a silicic acid chromatographic column followed by elution with ethyl acetate in benzene to afford, as an oil, methyl 7-(3(RS)-hydroxy-5-oxocyclopent-1-ene)hept-5-cis-enoate. It exhibits nuclear magnetic resonance maxima at $\delta 3.68$, $\delta 5.57$, and $\delta 7.19$.

EXAMPLE 10

To a solution of 0.288 part of methyl 7-(3(RS) hydroxy-5-oxocyclopent-1-ene)hept-5-cis-enoate in 3.6 parts by volume of ether is added 0.01 part of p-toluenesulfonic acid and 0.109 part of dihydropyran. The reaction mixture is allowed to stand at room temperature for about 24 hours, then in diluted with ether, washed successively with 5% aqueous potassium carbonate and water, dried over anhydrous sodium sulfate, and stripped of solvent under reduced pressure. The resulting product is methyl 7-(3(RS)-tetrahydropyran-2-yloxy-5-oxocyclopent-1-ene)hept-5-cis-enoate.

EXAMPLE 11

A mixture consisting of 5 parts of 1-octyn-4(RS)-ol, 6.6 parts of tertiary-butyldimethylsilyl chloride, 6.8 parts of imidazole and 10 parts by volume of dimethylformamide is stirred at room temperature for about 16 hours, then is poured into ether. The resulting organic solution is washed several times with water, then dried over anhydrous sodium sulfate and stripped of solvent under reduced pressure to afford 1-octyn-4(RS)-ol tertiary-butyldimethylsilyl ether, which exhibits a nuclear magnetic resonance maximum at $\delta 0.9$.

A mixture consisting of 2.4 parts of 1-octyn-4(RS)-ol tertiary-butyldimethylsilyl ether and 1.3 parts of catechol borane is warmed at 60°–70° for about 5 hours, then cooled and poured into cold water. The resulting aqueous mixture is stirred vigorously for about 15 minutes, then extracted with ether. The ether layer is separated, then washed several times with dilute aqueous potassium hydroxide and stripped of solvent under reduced pressure. The resulting residue is extracted with hexane and the hexane extract is washed twice with a solution consisting of 35 parts of potassium hydroxide dissolved in 25 parts of water and 100 parts by volume of methanol. Those alkaline extracts are combined, cooled to 0°–5°, then carefully acidified by the addition of dilute hydrochloric acid. That acidic solution is extracted with ether and the ether extract is washed with water, dried over anhydrous sodium sulfate and stripped of solvent by distillation under reduced pressure, thus affording, as a brown viscous oil, 4(RS)-tertiary-butyldimethylsilyloxy-trans-1-octenyl boronic acid, which displays a nuclear magnetic resonance maximum at $\delta 2.35$.

To a solution of 1.16 parts of 4(RS)-tertiary-butyldimethylsilyloxy-trans-1-octenyl boronic acid dissolved in 10 parts of methanol is added, at 0°, a solution consisting of 0.32 part of sodium hydroxide dissolved in 3 parts of water. To that cold mixture is then added dropwise a solution of 1.01 parts of iodine dissolved in 20 parts by volume of methanol. After the addition is complete, the mixture is diluted with ether, washed with water and dried over anhydrous sodium sulfate. Removal of the solvent by distillation under reduced pressure affords 4(RS)-tertiary-butyldimethylsilyloxy-trans-1-octenyl iodide, characterized by nuclear magnetic resonance maxima at $\delta 6.0$, $\delta 6.5$, and $\delta 2.2$.

EXAMPLE 12

To a solution of 3.7 parts of 4(RS)-tertiary-butyldimethylsilyloxy-trans-1-octenyl iodide in 10 parts by volume of ether, in a nitrogen atmosphere, is added, at $-60°$, 4.7 parts by volume of a 2.14 M n-butyl lithium solution in hexane. That mixture is stirred for about 30 minutes, at the end of which time a solution consisting of 4.46 parts of copper 1-pentynilide bis-hexamethylphosphorous triamide (prepared from copper 1-pentynilide and hexamethylphosphorous triamide) dissolved in 10 parts by volume of ether is added with stirring. Stirring is continued for 10 minutes, at the end of which time a solution consisting of 1.6 parts of methyl 7-(3(RS)-tetrahydropyran-2-yloxy-5-oxocyclopent-1-ene)heptanoate dissolved in 5 parts by volume of ether is added dropwise. That reaction mixture is stirred at about $-60°$ for approximately 2 hours, then at about $-40°$ for an additional hour. The reaction mixture is partitioned between ether and dilute hydrochloric acid and the ether layer is separated, washed with water, filtered, dried over anhydrous sodium sulfate, and stripped of solvent by distillation under reduced pressure. The resulting residue is purified by chromatography on a silica gel column, using 5% ethyl acetate and benzene as the eluant. Removal of the solvent from the eluate affords racemic methyl 7-[3(R)-(tetrahydropyran-2-yloxy)-2β-(4(RS)-tertiary-butyldimethylsilyloxy-trans-1-octenyl)-5-oxocyclopentane]-1α-heptanoate.

A solution consisting of 2 parts of the latter compound dissolved in 50 parts by volume of a 3:1:1 acetic acid:water:tetrahydrofuran mixture is allowed to stand at room temperature for about 16 hours, then is diluted with ether. The ether solution is washed several times with water, then dried over anhydrous sodium sulfate, stripped of solvent under reduced pressure and purified by chromatography on a silica gel column, using 60% ethyl acetate in hexane as the eluant. That eluate affords, as a yellow oil, racemic methyl 7-[3(R)-hydroxy-2β-(4(RS)-hydroxy-trans-1-octenyl)-5-oxocyclopentane]-1α-heptanoate. This compound is characterized by nuclear magnetic resonance spectrum peaks at δ0.9, δ2.73, δ3.68 and δ4.06.

The latter isomeric mixture is separated by high pressure liquid chromatography to afford racemic methyl 7-[3(R)-hydroxy-2β-(4(R)-hydroxy-trans-1-octenyl)-5-oxocyclopentane]-1α-heptanoate and racemic methyl 7-[3(R)-hydroxy-2β-(4(S)-hydroxy-trans-1-octenyl)-5-oxocyclopentane]-1α-heptanoate.

EXAMPLE 13

A mixture consisting of 2.8 parts of 4(RS)-4-methyl-1-octyn-4-ol, 3.5 parts of triethylsilyl chloride, 10 parts by volume of dimethylformamide and 3 parts by volume of triethylamine is heated at the reflux temperature for about 16 hours, then is cooled and diluted with ether. That organic solution is then washed successively with dilute hydrochloric acid and water, dried over anhydrous sodium sulfate and stripped of solvent under reduced pressure. Adsorption of the residue on a silica gel chromatographic column followed by elution with hexane affords 4(RS)-4-methyl-1-octyn-4-ol triethylsilyl ether, characterized by a nuclear magnetic resonance maximum at δ2.3.

To a solution of 1.27 parts of 4(RS)-methyl-1-octyn-4-ol triethylsilyl ether in 10 parts by volume of hexane is added, in a nitrogen atmosphere, at about 0°, 4 parts of a 20% diisobutyl aluminum hydride solution in toluene. The resulting reaction mixture is allowed to stand at room temperature for about 16 hours, then is warmed at about 60° for 2 hours. After cooling, the solution is partially concentrated, then diluted with approximately 5 parts by volume of tetrahydrofuran and cooled to about 0°. To that mixture is then added dropwise a solution consisting of 1.25 parts of iodine dissolved in 5 parts by volume of tetrahydrofuran. After the addition is complete, the mixture is partitioned between ether and hydrochloric acid. The ether layer is separated, washed successively with dilute aqueous sodium sulfite and water, then dried over anhydrous sodium sulfate and stripped of solvent under reduced pressure. The resulting residue is purified by chromatography on a silica gel column followed by elution with hexane, thus affording 4(RS)-4-methyl-4-triethylsilyloxy-trans-1-octenyl iodide. This compound is characterized by nuclear magnetic resonance spectrum peaks at about δ1.15 and δ5.95.

EXAMPLE 14

When an equivalent quantity of 4(RS)-4-methyl-4-triethylsilyloxy-trans-1-octenyl iodide is substituted in the procedure of Example 12, there is produced racemic methyl 7-[3(R)-hydroxy-2β-(4(RS)-4-hydroxy-4-methyl-trans-1-octenyl)-5-oxocyclopentane]-1α-heptanoate, characterized by nuclear magnetic resonance peaks of δ0.93, δ1.21 and δ4.07.

EXAMPLE 15

When an equivalent quantity of methyl 7-(3(RS)-tetrahydropyran-2-yloxy-5-oxocyclopent-1-ene)hept-5-cis-enoate is substituted in the procedure of Example 12, there are obtained racemic methyl 7-[3(R)-hydroxy-2β-(4(R)-hydroxy-trans-1-octenyl)-5-oxocyclopentane]-1α-hept-5-cis-enoate and racemic methyl 7-[3(R)-hydroxy-2β-(4(S)-hydroxy-trans-1-octenyl)-5-oxocyclopentane]-1α-hept-5-cis-enoate.

EXAMPLE 16

A mixture consisting of 25 parts of racemic methyl 7-[3(R)-hydroxy-2β-(4(S)-hydroxy-trans-1-octenyl)-5-oxocyclopentane]-1α-heptanoate, 10 parts of acetic anhydride and 10 parts of pyridine is allowed to stand at room temperature for about 16 hours, then is poured carefully into cold excess aqueous citric acid. The resulting aqueous mixture is allowed to stand at room temperature for about 1 hour, then is extracted several times with ether. The combined ether extracts are washed with cold water, dried over anhydrous sodium sulfate and concentrated under reduced pressure. The resulting residue is purified by adsorption on a silicic acid chromatographic column followed by elution with ethyl acetate in benzene, thus affording racemic methyl 7-[3(R)-acetoxy-2β-(4(S)-acetoxy-trans-1-octenyl)-5-oxocyclopentane]-1α-heptanoate.

EXAMPLE 17

To a solution of 2 parts of 4(RS)-4-methyl-1-octyn-4-ol triethylsilyl ether in approximately 10 parts by volume of hexane is added, at −30°, 7 parts of a 20% diisobutylaluminum hydride in toluene solution and the resulting reaction mixture is allowed to stand at room temperature for about 16 hours, then is warmed at about 60° for 2 hours, cooled to −60° and 0.96 part of methyl 3-hydroxy-5-oxocyclopent-1-eneheptanoate dissolved in 10 parts by volume of ether is added. Stirring at −60° is continued for 2–3 hours. The reaction mixture is then partitioned between ether and 1 N hydrochloric acid and the ether layer is separated, washed with water, dried over anhydrous sodium sulfate and stripped of solvent under reduced pressure. Chromatography on a silica gel column followed by elution with 10% ethyl acetate in benzene affords racemic methyl 7-[3(S)-hydroxy-2β-(4(RS)- 4-methyl-4-triethylsilyloxy-trans-1-octenyl)-5-oxocyclopentane]-1α-heptanoate.

The latter product is dissolved in a 3:1:1 acetic acid:water:tetrahydrofuran solution and kept at room temperature for about 16 hours, following which period of time the reaction mixture is extracted with ether. The ether layer is washed several times with water, dried over anhydrous sodium sulfate and stripped of solvent. The residue is then chromatographed on a silica gel column to afford racemic methyl 7-[3(S)-hydroxy-2β-(4(RS)-4-methyl-4-hydroxy-trans-1-octenyl)-5-oxocyclopentane]-1α-heptanoate.

EXAMPLE 18

The substitution of an equivalent quantity of 5,5-dimethyl-1-octyn-4(RS)-ol triethylsilyl ether in the procedure of Example 17 results in racemic methyl 7-[3(S)-hydroxy-2β-(4(RS)-5,5-dimethyl-4-hydroxy-trans-1-octenyl)-5-oxocyclopentane]-1α-heptanoate, which displays nuclear magnetic resonance peaks at δ0.89, δ0.90, δ3.69 and δ4.36.

EXAMPLE 19

To a solution of 0.368 part of racemic methyl 7-[3(R)-hydroxy-2β-(4(RS)-hydroxy-trans-1-octenyl)-5-oxocyclopentane]-1α-heptanoate in approximately 5 parts by volume of tetrahydrofuran, cooled to −78°, is added dropwise 3.32 parts by volume of a 0.9 N lithium perhydro-9b-boraphenylhydride solution in tetrahydrofuran. The solution is stirred for about 20 minutes at −78°, then quenched with water and allowed to warm to room temperature. Extraction with ether affords an organic solution, which is washed with water, dried over anhydrous sodium sulfate and stripped of solvent under reduced pressure to afford the crude product. Purification of that crude product is effected by chromatography on silica gel followed by elution with ethyl acetate, thus affording racemic methyl 7-[3(R)-hydroxy-2β-(4(RS)-hydroxy-trans-1-octenyl)-5α-hydroxycyclopentane]-1α-heptanoate.

EXAMPLE 20

The substitution of an equivalent quantity of tetrahydropyran-2-yl 7-(3(RS)-tetrahydropyran-2-yloxy-5-oxocyclopent-1-ene)heptanoate in the procedure of Example 12 affords racemic 7-[3(R)-hydroxy-2β-(4(R)-hydroxy-trans-1-octenyl)-5-oxocyclopentane]-1α-heptanoic acid and racemic 7-[3(R)-hydroxy-2β-(4(S)-hydroxy-trans-1-octenyl)-5-oxocyclopentane]-1α-heptanoic acid.

EXAMPLE 21

To a solution of 2.4 parts of 1-octyn-4(RS)-ol tertiary-butyldimethylsilyl ether in approximately 15 parts by volume of ether, cooled to −40°, is added 4.7 parts by volume of 2.14 M n-butyl lithium in hexane and the mixture thus produced is stirred at room temperature for about 30 minutes, then is cooled to about −40° and 3.7 parts of 25% dimethylaluminum chloride in hexane is added. After that mixture is stirred at room temperature for about 30 minutes, a solution of 1.2 parts of methyl 7-(3(RS)-hydroxy-5-oxocyclopent-1-ene)heptanoate in 10 parts by volume of ether is added dropwise. Stirring at room temperature for 4–5 hours is followed by partition of the mixture between ether and dilute hydrochloric acid. The ether layer is separated, washed with water, dried over anhydrous sodium sulfate and stripped of solvent under reduced pressure. The resulting residue is dissolved in a 3:1:1 solution of acetic acid:water:tetrahydrofuran and allowed to stand at room temperature for about 16 hours. Extraction with ether affords an organic solution, which is washed with water, dried over anhydrous sodium sulfate, stripped to dryness under reduced pressure and adsorbed on a silica gel chromatographic column. Elution with 30% ethyl acetate in hexane affords racemic methyl 7-[3(S)-hydroxy-2β-(4(RS)-hydroxy-1-octynyl)-5-oxocyclopentane]-1α-heptanoate, characterized by nuclear magnetic resonance peaks at δ3.7 and δ4.45.

EXAMPLE 22

To a mixture of 43.5 parts of magnesium in 125 parts by volume of ether is added a portion of a solution containing 84 parts of methyl cyclohexylmethyl ketone and 71.4 parts of propargyl bromide in a solution consisting of 60 parts by volume of benzene and 180 parts by volume of ether. After the addition of 0.05 part of mercuric chloride to initiate the reaction, the remainder of the reactants is added dropwise. The reaction mixture is heated at the reflux temperature for about 15 minutes, allowed to cool to room temperature, then poured carefully into cold dilute hydrochloric acid. The aqueous phase is separated, extracted with ether and the combined ether extracts are washed successively with water, saturated aqueous sodium bicarbonate and saturated aqueous sodium chloride, dried over anhydrous sodium sulfate and evaporated to dryness. Vacuum distillation of the residue affords 4(RS)-4-cyclohexylmethyl-4-methyl-1-butyn-4-ol.

The substitution of an equivalent quantity of 4(RS)-4-cyclohexylmethyl-4-methyl-1-butyn-4-ol in the procedure of Example 13 results in 4(RS)-4-cyclohexylmethyl-4-methyl-1-butyn-4-ol triethylsilyl ether.

By substituting an equivalent quantity of 4(RS)-4-cyclohexylmethyl-4-methyl-1-butyn-4-ol triethylsilyl ether in the procedure of Example 13, 4(RS)-4-cyclohexylmethyl-4-methyl-4-triethylsilyloxy-trans-1-butenyl iodide is produced.

When an equivalent quantity of 4(RS)-4-cyclohexylmethyl-4-methyl-4-triethylsilyloxy-trans-1-butenyl iodide is substituted in the procedures of Example 12, there are obtained racemic methyl 7-[3(R)-(tetrahydropyran-2-yloxy)-2β-(4(RS)-4-cyclohexylmethyl-4-methyl-4-triethylsilyloxy-trans-1-butenyl)-5-oxocyclopentane]-1α-heptanoate and racemic methyl 7-[3(R)-hydroxy-2β-(4(RS)-4-cyclohexylmethyl)-4-hydroxy-4-methyl-trans-1-butenyl)-5-oxocyclopentane]-1α-heptanoate.

EXAMPLE 23

A solution consisting of 1 part of racemic methyl 7-[3(R)-hydroxy-2β-(4(RS)-hydroxy-trans-1-octenyl)-5-oxocyclopentane]-1α-heptanoate in 50 parts by volume of 90% acetic acid is warmed at about 60° under a nitrogen atmosphere for about 18 hours, then cooled, diluted with ether, washed with water, dried over anhydrous sodium sulfate and stripped to dryness to afford racemic methyl 7-[2β-(4(RS)-hydroxy-trans-1-octenyl)-5-oxocyclopent-3-ene]-1α-heptanoate, characterized by an ultraviolet absorption maximum at about 217 millimicrons with a molecular extinction coefficient of about 9,000.

EXAMPLE 24

A solution of 1.85 parts of 4(RS)-tertiary-butyldimethylsilyloxy-trans-1-octenyl iodide in 10 parts by volume of ether is cooled to about −60° and 2.33 parts by volume of a 2.14 M n-butyl lithium in hexane solution is added. That mixture is stirred for about 30 minutes, at the end of which time a solution of copper 1-pentynylide bis-hexamethylphosphorus triamide (prepared from 0.65 part of pentynyl copper and 1.63 parts of hexamethylphosphorus triamide) in 5 parts by volume of ether is added. The resulting mixture is stirred at −60° for 10 minutes and a solution of 0.75 part of tetrahydropyran-2-yl 5-oxocyclopent-1-eneheptanoate in 3 parts by volume of ether is added. That mixture is stirred first at −60° for 1 hour, then at −20° for an additional hour, then is diluted with ether. The ether solution is washed successively with dilute hydrochloric acid and water, then concentrated to dryness under reduced pressure. The residue is extracted with a 10:1:1 mixture of acetone:methanol:1 N hydrochloric acid and the extract is allowed to stand at room temperature for about 3 hours, then is diluted with ether and extracted with 5% aqueous potassium carbonate. The alkaline extract is washed with ether, acidified with dilute hydrochloric acid and extracted with ether. The resulting ether solution is washed with water, dried over anhydrous sodium sulfate and stripped of solvent under reduced pressure to afford racemic 7-[2β-(4(RS)-hydroxy-trans-1-octenyl)-5-oxocyclopentane]-1α-heptanoic acid, which displays a nuclear magnetic resonance peak at δ5.55.

EXAMPLE 25

The substitution of an equivalent quantity of racemic methyl 7-[3(R)-hydroxy-2β-(4(RS)-4-hydroxy-4-methyl-trans-1-octenyl)-5-oxocyclopentane]-1α-heptanoate in the procedure of Example 19 results in racemic methyl 7-[3(R)-hydroxy-2β-(4(RS)-4-hydroxy-4-methyl-trans-1-octenyl)-5α-hydroxycyclopentane]-1α-heptanoate, which displays nuclear magnetic resonance peaks at about δ0.91, δ1.16, δ3.67, δ3.91 and δ4.17.

EXAMPLE 26

A mixture containing 3 parts of 5,5-dimethyl-1-octyn-4(RS)-ol, 3.3 parts of triethylsilyl chloride, 3.4 parts of imidazole and 5 parts by volume of dimethylformamide is stirred at room temperature for about 1 hour, then is partitioned between water and ether. The ether solution is separated, washed several times with water, dried over anhydrous sodium sulfate and concentrated to dryness under reduced pressure to afford 5,5-dimethyl-1-octyn-4(RS)-ol triethylsilyl ether.

A mixture consisting of 2.68 parts of 5,5-dimethyl-1-octyn-4(RS)-ol triethylsilyl ether and 2 parts of catechol borane is kept in an atmosphere of nitrogen at room temperature for about 48 hours. The mixture is partitioned between water and hexane and the hexane layer is washed successively with aqueous potassium carbonate and aqueous potassium hydroxide, then extracted several times with a solution containing 35 parts of potassium hydroxide, 25 parts of water and 100 parts by volume of methanol. The latter alkaline extracts are combined, cooled to 0.5°, then acidified with dilute hydrochloric acid. Extraction of the acidic mixture with ether affords an organic solution, which is washed with water, dried over anhydrous sodium sulfate and concentrated to dryness under reduced pressure to afford 5,5-dimethyl-4(RS)-triethylsilyloxy-trans-1-octenyl boronic acid.

EXAMPLE 27

To a solution of 1.5 parts of 5,5-dimethyl-4(RS)-triethylsilyloxy-trans-1-octenyl boronic acid in 15 parts by volume of methanol is added a solution of 0.45 part of sodium hydroxide in 5 parts of water. To that mixture is then added dropwise, at about 0°, 1.5 parts of iodine dissolved in 30 parts of methanol. After completion of the addition, the reaction mixture is diluted with ether, washed successively with 1% aqueous sodium sulfite and water, dried over anhydrous sodium sulfate and stripped of solvent under reduced pressure. The resulting residue is purified by adsorption on a silica gel chromatographic column followed by elution with hexane, thus affording 5,5-dimethyl-4(RS)-triethylsilyloxy-trans-1-octenyl iodide.

EXAMPLE 28

When an equivalent quantity of 5,5-dimethyl-4(RS)-triethylsilyloxy-trans-1-octenyl iodide is substituted in the proecedure of Example 12, there are obtained racemic methyl 7-[3(R)-tetrahydropyran-2-yloxy)-2β-(5,5-dimethyl-4(RS)-triethylsilyloxy-trans-1-octenyl)-5-oxocyclopentane]-1α-heptanoate and racemic methyl 7-[3(R)-hydroxy-2β-(5,5-dimethyl-4(RS)-hydroxy-1-trans-octenyl)-5-oxocyclopentane]-1α-heptanoate.

Cleavage of the triethylsilyloxy group is achieved by the procedure of Example 12, thus affording the crude product, which is purified by adsorption on a silicic acid chromatographic column followed by elution with 2% ethanol in methylene chloride to yield racemic methyl 7-[3(R)-hydroxy-2β-(4(RS)-5,5-dimethyl-4-hydroxy-trans-1-octenyl)-5-oxocyclopentane]-1α-heptanoate, characterized by nuclear magnetic resonance peaks at δ0.87, δ0.89, δ3.68 and δ4.07, racemic methyl 7-[3(R)-hydroxy-2β-(5,5-dimethyl-4(S)-hydroxy-trans-1-octenyl)-5-oxocyclopentane]-1α-heptanoate and racemic methyl 7-[3(R)-hydroxy-2β-(5,5-dimethyl-4(R)-hydroxy-trans-1-octenyl)-5-oxocyclopentane]-1α-heptanoate.

EXAMPLE 29

The substitution of an equivalent quantity of 4(RS)-4-methyl-1-octyn-4-ol triethylsilyl ether in the procedure of Example 21 results in racemic methyl 7-[3(S)-hydroxy-2β-(4(RS)-4-hydroxy-4-methyl-1-octynyl)-5-oxocyclopentane]-1α-heptanoate.

EXAMPLE 30

To a solution of 6.8 parts of 3-methyl-1-butyne in 50 parts by volume of ether, cooled to −40°, is added dropwise 46.7 parts by volume of 2.14 M n-butyl lithium in hexane. The resulting solution is allowed to warm to room temperature and is stored at that temperature for about 15–30 minutes, then cooled again to −40° and 10.8 parts of trimethylsilyl chloride is added. The temperature is allowed to rise to room temperature and the mixture is stirred for about 1 hour, at the end of which time 46.7 parts by volume of 2.14 M n-butyl lithium in hexane is added dropwise. The resulting reaction mixture is heated at the reflux temperature for about 18 hours, then is cooled to about −10° and 8.6 parts of valeraldehyde is added. The mixture is allowed to warm to room temperature, then is stirred for about 2 hours and poured into a mixture of ether and dilute hydrochloric acid. The ether layer is washed with water, dried over anhydrous sodium sulfate, stripped of solvent under reduced pressure and distilled under vacuum to afford (4(RS)-hydroxy-3,3-dimethyl-1-octynyl)trimethylsilane, characterized by an infrared absorption maximum of about 2160 reciprocal centimeters.

A mixture of 1 part of (4(RS)-hydroxy-3,3-dimethyl-1-octynyl)trimethylsilane, 1 part of potassium fluoride and 5 parts by volume of dimethylformamide is stirred vigorously at room temperature for about 16 hours, then is diluted with ether and water. The ether layer is separated, washed with water, dried over anhydrous sodium sulfate and stripped of solvent under reduced pressure to afford 3,3-dimethyl-1-octyn-4(RS)-ol, which exhibits an infrared absorption maximum at about 3320 reciprocal centimeters.

When an equivalent quantity of 3,3-dimethyl-1-octyn-4(RS)-ol is subjected to the successive process of Examples 26 and 27, there is produced 3,3-dimethyl-4(RS)-triethylsilyloxy-trans-1-octenyl iodide.

The substitution of an equivalent quantity of 5,5-dimethyl-4(RS)-triethylsilyloxy-trans-1-octenyl iodide in the procedure of Example 12 results in racemic methyl 7-[3(R)-hydroxy-2β-(4(RS)-3,3-dimethyl-4-hydroxy-trans-1-octenyl)-5-oxocyclopentane]-1α-heptanoate.

EXAMPLE 31

A solution consisting of 0.096 part of methyl 7-[3(R)-hydroxy-2β-(4(RS)-4-hydroxy-4-methyl-trans-1-octenyl)-5-oxocyclopentane]-1α-heptanoate in 20 parts by volume of isopropyl alcohol is shaken with hydrogen at room temperature and atmospheric pressure in the presence of 0.02 part of 5% palladium-on-carbon catalyst until 1 molecular equivalent of hydrogen is absorbed. The solution is then filtered to remove the catalyst and the filtrate is concentrated to dryness, thus affording methyl 7-[3(R)-hydroxy-2β-(4(RS)-4-hydroxy-4-methyloctyl)-5-oxocyclopentane]-1α-heptanoate.

EXAMPLE 32

A mixture consisting of 6.3 parts of 1-octyn-4(RS)-ol, 7.4 parts of phthalic anhydride and 10 parts by volume of pyridine is heated at the reflux temperature for about 3 hours, then allowed to cool for about 16 hours. At the end of that time the mixture is diluted with ether, then is washed with dilute hydrochloric acid. Extraction with dilute sodium hydroxide, followed by acidification of the alkaline extract affords an aqueous solution which is then extracted with ether. The ether extract is dried over anhydrous sodium sulfate, decolorized with activated carbon and stripped of solvent to afford 1-octyn-4(RS)-ol phthalate.

A mixture of 2.24 parts of 1-octyn-4(RS)-ol phthalate and 0.99 part of 1(—)-α-methylbenzylamine dissolved in 125 parts by volume of methylene chloride is stirred for about 10 minutes, then is partially concentrated under reduced pressure. The mixture is diluted with ether and cooled, resulting in crystallization of the diastereomeric amine salts. Fractional crystallization from cyclohexane affords 1-octyn-4(S)-ol phthalate, melting at about 110°–112°.

A mixture consisting of 1.07 parts of the latter salt, 10 parts by volume of 1 N sodium hydroxide and 10 parts by volume of methanol is heated at about 60° for about 90 minutes, then is cooled to room temperature and diluted with hexane. The hexane layer is separated, washed with water, dried over anhydrous sodium sulfate and stripped of solvent to afford 1-octyn-4(S)-ol, characterized by an optical rotation of —46.5° in ether at 24°C.

EXAMPLE 33

A mixture consisting of 0.24 part of methyl 3(RS)-hydroxy-5-oxocyclopent-1-ene heptanoate, 0.2 part of 2(S)-aminoxyisocaproic acid and 4 parts of methanol is treated with 0.5 part of pyridine. The resulting mixture is allowed to stand at room temperature for about 16 hours, then is poured into a mixture consisting of 45 parts of ethyl acetate and 20 parts by volume of 0.5 N hydrochloric acid. The ethyl acetate layer is separated, washed with water and dried over anhydrous sodium sulfate. The solvent is removed by evaporation under reduced pressure and the residue is chromatographed on a silica gel column using 1% ethyl acetate in chloroform as the eluant, thus affording, successively, methyl 3(R)-hydroxy-5-[(1-carboxyisoamyl)oxyimino]cyclopent-1-eneheptanoate, melting at about 62°–63°, and methyl 3(S)-hydroxy-5-[(1-carboxyisoamyl)oxyimino]cyclopent-1-eneheptanoate.

Each of the above oximes is mixed with 1.5 parts of ammonium acetate, 1 part of acetic acid, 10 parts of water, 27 parts of tetrahydrofuran and 3 parts by volume of an aqueous 20% titanium trichloride solution and stirred at 60° for about 16 hours under a nitrogen atmosphere. Each mixture is diluted with ether and extracted with water. The ether layer is separated, washed successively with aqueous 2% sodium bicarbonate and water, dried over anhydrous sodium sulfate and stripped of solvent under reduced pressure to yield, respectively, methyl 3(R)-hydroxy-5-oxocyclopent-1-eneheptanoate and methyl 3(S)-hydroxy-5-oxocyclopent-1-eneheptanoate.

EXAMPLE 34

When an equivalent quantity of 1-octyn-4(S)-ol is subjected to the successive processes of Examples 26 and 27, there is produced 4(S)-triethylsilyloxy-trans-1-octenyl iodide.

EXAMPLE 35

The substitution of equivalent quantities of methyl 7-[3(R)-tetrahydropyran-2-yloxy-5-oxocyclopent-1-ene]heptanoate and 4(S)-triethylsilyloxy-trans-1-octenyl iodide in the procedures of Example 12 results in methyl 7-[3(R)-hydroxy-2β-(4(S)-hydroxy-trans-1-octenyl)-5-oxo-cyclopentane]-1α-heptanoate.

EXAMPLE 36

When equivalent quantities of methyl 7-[3(S)-tetrahydropyran-2-yloxy-5-oxocyclopent-1-ene]heptanoate and 4(S)-triethylsilyloxy-trans-1-octenyl iodide are substituted in the procedures of Example 12, there is obtained methyl 7-[3(S)-hydroxy-2β-(4(S)-hydroxy-trans-1-octenyl)-5-oxocyclopentane]-1α-heptanoate.

EXAMPLE 37

To a solution of 1.26 parts of 1-octyn-4(RS)-ol in 10 parts by volume of ethylene glycol dimethyl ether, cooled to about —40° is added dropwise 4 parts by volume of 2.5 M n-butyl lithium in hexane. The cooling bath is removed and 4 parts of trimethyloxonium hexafluorophosphate is added. The resulting reaction mixture is stirred at room temperature for about 1 hour, then is diluted with ether, washed successively with dilute hydrochloric acid and water, dried over anhydrous sodium sulfate and stripped of solvent under reduced pressure to afford 1-octyn-4(RS)-ol methyl ether.

EXAMPLE 38

When an equivalent quantity of 1-octyn-4(RS)-ol methyl ether is subjected to the successive processes described in Examples 11 and 12, there is produced racemic methyl 7-[3(R)-hydroxy-2β-(4(RS)-methoxy-trans-1-octenyl)-5-oxocyclopentane]-1α-heptanoate.

EXAMPLE 39

A solution consisting of 11.6 parts of 4(RS)-tertiary-butyldimethylsilyloxy-trans-1-octenylboronic acid and 40 parts by volume of methylene chloride is cooled to —20° and 6.4 parts of bromine is added dropwise. After the reaction mixture is stirred for about 1 hour, a solution of 2.16 parts of sodium methoxide in 20 parts by volume of methanol is added and stirring is continued for an additional hour. The mixture is allowed to warm to room temperature, then is diluted with ether, washed with water, dried over anhydrous sodium sulfate and stripped of solvent under reduced pressure. The crude product is purified by adsorption on a silica gel chromatographic column followed by elution with hexane, thus affording 4(RS)-tertiary-butyldimethylsilyloxy-cis-1-octenyl bromide.

EXAMPLE 40

EXAMPLE 40

When an equivalent quantity of 4(RS)-tertiary-butyldimethylsilyloxy-cis-1-octenyl bromide is substituted in the procedure of Example 12, there is obtained racemic methyl 7-[3(R)-hydroxy-2β-(4(RS)-hydroxy-cis-1-octenyl)-5-oxocyclopentane]-1α-heptanoate.

EXAMPLE 41

A mixture consisting of 1 part of racemic methyl 7-[3(R)-hydroxy-2β-(4(RS)-4-hydroxy-4-methyl-trans-1-octenyl)-5α-hydroxycyclopentane]-1α-heptanoate, 10 parts by volume of 5% aqueous potassium carbonate and 10 parts by volume of methanol is allowed to stand at room temperature for about 16 hours, then is acidified by the addition of hydrochloric acid and extracted with ethyl acetate. The organic layer is separated, washed with water, dried over anhydrous sodium sulfate and evaporated to dryness to afford racemic 7-[3(R)-hydroxy-2β-(4(RS)-4-hydroxy-4-methyl-trans-1-octenyl)-5α-hydroxycyclopentane]-1α-heptanoic acid.

EXAMPLE 42

When an equivalent quantity of racemic methyl 7-[3-(R)-hydroxy-2β-(4(RS)-4-hydroxy-4-methyl-trans-1-octenyl)-5-oxocyclopentane]-1α-heptanoate is substituted in the procedure of Example 23, there is obtained racemic methyl 7-[2β-(4(RS)-4-hydroxy-4-methyl-trans-1-octenyl)-5-oxocyclopent-3-ene]-1α-heptanoate.

EXAMPLE 43

The substitution of an equivalent quantity of racemic methyl 7-[3(R)-hydroxy-2β-(4(RS)-4-cyclohexylmethyl-4-methyl-4-hydroxy-trans-1-butenyl)-5-oxocyclopentane]-1α-heptanoate in the procedure of Example 23 results in racemic methyl 7-[2β-(4(RS)-4-cyclohexylmethyl-4-methyl-4-hydroxy-trans-1-butenyl)-5-oxocyclopent-3-ene]-1α-heptanoate.

EXAMPLE 44

To a solution of 3.8 parts of racemic methyl 7-[3(R)-hydroxy-2β-(4(RS)-4-hydroxy-4-methyl-trans-1-octenyl)-5-oxocyclopentane]-1α-heptanoate in 100 parts by volume of ethanol is added 0.4 part of sodium borohydride and the resulting reaction mixture is stirred at room temperature for about 10 minutes, then diluted with ether, washed successively with dilute hydrochloric acid and water, dried over anhydrous sodium sulfate and concentrated to dryness to afford the crude product. Purification by adsorption on a silica gel chromatographic column followed by elution with ethyl acetate affords, successively, racemic methyl 7-[3(R)-hydroxy-2β-(4(RS(-4-hydroxy-4-methyl-trans-1-octenyl)-5α-hydroxycyclopentane]-1α-heptanoate and racemic methyl 7-[3(R)-hydroxy2β-(4(RS)-4-hydroxy-4-methyl-trans-1-octenyl)-5β-hydroxycyclopentane]-1α-heptanoate.

What is claimed is:

1. The compound which is racemic methyl 7-[3(R)-hydroxy-2β-(4(RS)-4-hydroxy-4-methyl-trans-1-octenyl)-5-oxocyclopentane]-1α-heptanoate.

2. The compound which is racemic methyl 7-[3(S)-hydroxy-2β-(4(RS)-4-hydroxy-4-methyl-1-octynyl)-5-oxocyclopentane]-1α-heptanoate.

3. The compound which is racemic methyl 7-[3(R)-hydroxy-2β-(4(RS)-4-cyclohexylmethyl-4-hydroxy-4-methyl-trans-1-butenyl)-5-oxocyclopentane]-1α-heptanoate.

* * * * *

UNITED STATES PATENT AND TRADEMARK OFFICE

CERTIFICATE EXTENDING PATENT TERM
UNDER 35 U.S.C. 156

Patent No.    : 3,965,143

Dated         : June 22, 1976

Inventor(s)   : PAUL W. COLLINS ET AL

Patent Owner  : G.D. SEARLE & CO.

This is to certify that there has been presented to the

COMMISSIONER OF PATENTS AND TRADEMARKS an application under 35 U.S.C. 156 for an extension of the patent term. Since it appears that the requirements of the law have been met, this certificate extends the term of the patent for the period of

2 YEARS with all rights pertaining thereto as provided by 35 USC 156 (b).

I have caused the seal of the Patent and Trademark Office to be affixed this 11th day of December 1989.

Jeffrey M. Samuels
Acting Commissioner of
  Patents and Trademarks